United States Patent [19]
Kaul et al.

[11] Patent Number: 5,961,459
[45] Date of Patent: Oct. 5, 1999

[54] USE OF HOLLOW MICROCAPSULES IN DIAGNOSIS AND THERAPY

[75] Inventors: Sanjiv Kaul, Charlottesville, Va.; Richard Alan Johnson, Ruddington, United Kingdom

[73] Assignee: Andaris Limited, United Kingdom

[21] Appl. No.: 08/953,513

[22] Filed: Oct. 17, 1997

[30] Foreign Application Priority Data

Oct. 19, 1996 [GB] United Kingdom .................. 9621826
Oct. 19, 1996 [GB] United Kingdom .................. 9621833

[51] Int. Cl.⁶ ...................................................... A61B 8/00
[52] U.S. Cl. .............................................................. 600/439
[58] Field of Search .................................... 600/439, 458, 600/462, 463, 466, 467, 469; 607/105, 120; 424/9.5, 9.51, 9.52

[56] References Cited

U.S. PATENT DOCUMENTS

| | | | |
|---|---|---|---|
| 4,315,435 | 2/1982 | Proudina | 73/628 |
| 5,069,936 | 12/1991 | Yen | 427/213.33 |
| 5,199,951 | 4/1993 | Spears | 607/105 |
| 5,518,709 | 5/1996 | Sutton et al. | 424/9.52 |

FOREIGN PATENT DOCUMENTS

| | | |
|---|---|---|
| WO 91/12823 | 9/1991 | WIPO . |
| WO 92/18164 | 10/1992 | WIPO . |
| WO 94/08627 | 4/1994 | WIPO . |
| WO 96/09814 | 4/1996 | WIPO . |
| WO 96/15814 | 5/1996 | WIPO . |
| WO 96/18388 | 6/1996 | WIPO . |

OTHER PUBLICATIONS

Zhang, Y. Y. et al., "Nitrosation of Tryptophan Residue(s) in Serum Albumin and Model Dipeptides," *J. Biol. Chem.* 271 (24):14271–14279 (1996).

*Primary Examiner*—George Manuel
*Attorney, Agent, or Firm*—Sterne, Kessler, Goldstein & Fox P.L.L.C.

[57] ABSTRACT

A diagnostic method analyses the effect of intervention, e.g. by surgery, especially in the myocardium. (i) Hollow microcapsules are administered into a blood vessel of a patient having a perfusion defect, (ii) if desired, an ultrasonic image is formed of the tissue, (iii) the occlusion is at least partially removed such that the blood flow in at least one area of the tissue is increased, and (iv) an ultrasonic image of the tissue is obtained after treatment. This is based on the observation of the particular properties of the microcapsules in the myocardium. It is also the basis of providing appropriate drugs to that site.

23 Claims, No Drawings

USE OF HOLLOW MICROCAPSULES IN DIAGNOSIS AND THERAPY

FIELD OF THE INVENTION

The present invention relates to the use of hollow microcapsules in ultrasound imaging and in therapy.

BACKGROUND OF THE INVENTION

Narrowing and occlusion of the coronary arteries constitute one of the major causes of heart disease. Coronary artery disease leads to perfusion defects which in turn lead to myocardial infarction.

Currently, the only reliable method for the detection of myocardial perfusion abnormalities is nuclear imaging. However, this imaging technique is relatively expensive and takes several hours to complete. By far the most widely used imaging method in cardiac examination is ultrasonography. However, at present, it is not possible to determine myocardial perfusion abnormalities with this imaging method.

The evaluation of myocardial perfusion is particularly important before and after interventional procedures. The determination of the restoration of myocardial blood flow after intervention is a critical factor in confirming the success of this procedure.

Various echo contrast agents are currently in clinical development. However, these agents provide only transient images of myocardial perfusion and they suffer from problems such as attenuation. The perfusion images generated are of insufficient duration to allow the clinician to generate accurate 3-D reconstructions.

A further disadvantage of existing intravenous (IV) agents is that myocardial perfusion images require the use of harmonic, triggered imaging techniques. At present, few suitable machines are available. Further, triggered images fail to generate real time images. Therefore, it is not possible to generate moving images of the myocardium whilst visualising echocontrast.

Ultrasound contrast agents can be introduced into the body to reflect or absorb ultrasound energy, or to resonate when exposed to such energy, and thereby provide an enhanced image of a part of the body. Examples of such contrast agents, in the form of hollow microcapsules, are given in WO-A-92/18164, WO-A-94/08627 and WO-A-96/15814. Such agents are injected into the patient's bloodstream and then the patient is subjected to ultrasound radiation.

SUMMARY OF THE INVENTION

It has now been found that the microcapsules of the type described in WO-A-9218164 can provide hitherto unavailable information on the perfusion profile of the myocardium and subsequent changes in the perfusion image (after interventional procedures), and this can be achieved without further administration of doses. The perfusion changes that are demonstrated after interventional therapy have been termed "reperfusion". This effect can be utilised in any capillary bed, and the microcapsules should be capable of retention there, i.e. usually no more than 20 μm in size.

The procedures of the present invention enable the clinician to obtain real time images of the success of interventional therapy without further administration of the agent. This is because, unlike the situation when other contrast agents are used, the contrast agents used in the present invention flow with the blood when the occlusion is removed, and delineate not only the original tissue but also the tissue which is newly exposed to the blood. More specifically, it has been demonstrated that air-filled albumin microcapsules produced by spray-drying and which have a median diameter of, say, 10–15 μm can be deposited in the heart or directly into the coronary arteries using intra-arterial catheter techniques. As the microcapsules reside in the myocardium for several hours, this allows high definition ultrasound images of the myocardium to be produced. Smaller microparticles may also be useful.

In general terms, the invention may be characterised as, a diagnostic method which comprises (i) administering the hollow microcapsules into a blood vessel of a patient having a perfusion defect (for example a partial or complete occlusion of blood flow to the tissue), (ii) if desired, obtaining an ultrasonic image of the tissue affected by the defect, (iii) treating the patient and thereby, removing the said occlusion at least partially, such that the blood flow in at least one area of the tissue is increased, and (iv) obtaining an ultrasonic image of the tissue post-treatment.

Preferably, further ultrasonic images are obtained (advantageously, they are obtained substantially continuously) post-treatment, or between steps (ii) and (iv); the imaging may therefore be a "real time" visualisation of the tissue before, during and after the surgical or therapeutic intervention in step (iii). There is no need for further contrast agent to be administered.

According to a second aspect of the invention, a drug is incorporated or linked within, into or onto the microcapsule. An imaging agent with therapeutic utility at a particular locus is thus provided. Such microparticles are particularly useful in therapy by being, or having associated therewith, a therapeutic agent whose effect is mediated by application to the heart or coronary vessels.

Diagnosis according to this invention allows both evaluation of a risk area, and evaluation of perfusion rather than blood flow. If a therapeutic agent is used, it can be delivered effectively to the risk area.

DESCRIPTION OF THE INVENTION

The tissue is preferably cardiac tissue (especially the myocardium) but may alternatively be any other organ, for example the kidney, liver or brain. The contrast agent is normally delivered via a catheter upstream of the organ to be perfused. Suitably, for imaging cardiac tissue, the contrast agent is administered directly into the left atrium, left ventricle, aortic root or coronary artery. Delivery into the hepatic artery can be used for procedures in the liver; intravenous administration for the lung.

The microcapsules may be made by the method of WO-A-92/18164 (U.S. Pat. No. 5,518,709) or WO-A-9408627, the contents of which are incorporated herein by reference. More specifically, any of the wall-forming materials and additives disclosed in those documents may be used, as may any suitable sizes of microcapsules disclosed in those documents. Microcapsules smaller than 6 μm may not deposit on the tissue walls so effectively, whereas microcapsules larger than 20 μm may lodge higher in the capillary network and may not reperfuse in the microcirculation. Of course, such larger and smaller microcapsules may be included in the composition, for whatever reason, but they will generally not contribute to the present invention. Hence, for example, the microcapsules can have a size range of 0.1–8 μm with a median of about 3 μm or a size range of 1–20 μm with a median of about 6–15 μm, e.g. 10–13 μm. (The size ranges refer to at least 90% of the microcapsules, as measured by volume on a Coulter Multisizer II with a 70 μm aperture tube.)

The microcapsules are suitable for use as a deposit echocontrast agent, to delineate under-perfused areas of microcirculation. It has been found that microcapsules of mean size 12–15 μm have echogenicities some $4.6 \times 10^4$ fold higher than similar microcapsules of mean size 5 μm. Hence, a relatively low dose can be used to image regions deep inside the body which are inaccessible to normal ultrasound techniques. A typical population of such large microcapsules has a mean size of 12 μm and 85% lying in the diameter range 9–18 μm.

Due to the pressure stability of the preferred microcapsules, they retain air and hence echogenicity for a substantial period of time. The microcapsules may deposit in the vasculature following catheter administration in a manner similar to classical microcapsule studies, reflecting the amount of flow to any given perfusion territory. Imaging of the territory may then be made after catheter withdrawal and patient stabilisation, to enable more optimal images in multiple planes to be gathered. Comparison with a baseline unenhanced image thus enables the perfusion, following a corrective procedure, to be assessed.

The microcapsules may be tailored for intracoronary use not only by manipulation of their size and pressure stability but also by their rate of biodegradation. In addition, it is preferable if the walls of the microcapsules are negatively charged at physiological pH.

For intracoronary use, it is preferable to cross-link the large (10–20 μm) microcapsules at 175° C. for a period of 18–60 minutes, more preferably 20–40 minutes and most preferably 35–40 minutes. This yields microcapsules that are pressure-resistant but have a shortened tissue half-life compared to the microcapsules of WO-A-9218164 and therefore are more applicable to use in the microcirculation of the myocardium. The tissue half-life can be measured by labelling the microcapsules with $^{125}I$ by the Chloramine T method, and assessing the organ content of microcapsules by necropsy or the release of $^{125}I$ into the urine and faeces.

Preferably, the microcapsules are made using the materials and methods described in WO-A-96/15814; see in particular page 1 line 28 to page 12 line 24. The method generally comprises spraying an aqueous solution of a water-soluble material with a water-miscible organic solvent into a gas such that the aqueous solvent evaporates, thereby forming hollow microcapsules, wherein the aqueous solution contains a liquid of greater volatility than water.

The microcapsules for use in this invention are generally larger than those preferred in WO-A-9615814; therefore, the aqueous solution or dispersion for spray-drying preferably contains 5 or 10–30% w/v protein, particularly when the material is albumin.

Preferably, the steps of resuspending the product and then freeze-drying the suspension, which are options in WO-A-9615814, are not performed. The microcapsules are simply milled with any desired additives (e.g. lactose) and filled into final containers.

The product is hence generally supplied and stored as a dry powder and is suspended in a suitable sterile, non-pyrogenic liquid just before administration. The suspension is generally administered by injection of about 0.05–15 ml into a suitable vein, such as the cubital vein or other blood vessel, if the microcapsules are of relatively small size (up to about 8 μm). Otherwise, for larger sizes, the suspension must be delivered into an artery. A microcapsule concentration of about $1 \times 10^5$ to $1 \times 10^{12}$ particles/ml is suitable, preferably about $5 \times 10^5$ to $5 \times 10^9$. The number of microcapsules administered can therefore be from $5 \times 10^3$ to $5 \times 10^{12}$.

Typically, a dose of 1–5 ml, containing $1.5 \times 10^7$ microcapsules, 6–15 μm in diameter, per ml, is used. For delivery into the coronary artery, a dose of 0.1–0.5 ml is sufficient.

Although the ultrasonic imaging method of the invention is applicable to various animal and human body organ systems, one of its main applications is in obtaining images of myocardial tissue and perfusion or blood flow patterns.

The techniques use ultrasonic scanning equipment consisting of a scanner and imaging apparatus. The equipment produces visual images of a predetermined area, for example the heart region of a human body. Typically, the transducer is placed directly on the skin over the area to be imaged. The scanner houses various electronic components including ultrasonic transducers. The transducer produces ultrasonic waves which perform a sector scan of the heart region. The ultrasonic waves are reflected by the various portions of the heart region and are received by the receiving transducer and processed in accordance with pulse-echo methods known in the art. After processing, signals are sent to the imaging apparatus (also well known in the art) for viewing.

In the method of the present invention, after the patient is "prepped" and the scanner is in place, the microcapsule suspension is injected.

With these microcapsules, observations and diagnoses can be made with respect to the amount of time required for the blood to pass through the lungs, blood flow patterns, the size of the left atrium, the competence of the mitral valve (which separates the left atrium and left ventricle), chamber dimensions in the left ventricular cavity and wall motion abnormalities. Upon ejection of the contrast agent from the left ventricle, the competence of the aortic valve also may be analyzed, as well as the ejection fraction or percentage of volume ejected from the left ventricle. Finally, the contrast patterns in the tissue will indicate which areas, if any, are not being adequately perfused.

In summary, such a pattern of images will help diagnose unusual blood flow characteristics within the heart, valvular competence, chamber sizes and wall motion, and will provide a potential indicator of myocardial perfusion.

The microcapsules may permit left heart imaging from intravenous injections. The smaller sizes of albumin microcapsules, when injected into a peripheral vein, may be capable of transpulmonary passage. This results in echocardiographic opacification of the left ventricle (LV) cavity as well as myocardial tissue.

The reperfusion event can be visualised with a broad range of imaging machines and ultrasound probes. For example the reperfusion of the microcapsules can be determined using the ATL 3000 HDI imaging machine. Imaging the reperfusion event is possible using either the P5-3 or the P3-2 ultrasound probe in either the fundamental or the harmonic mode.

Other imaging machines that can be used include the HP Sonus 1500, 2000 or 2500 (harmonic/fundamental), Vingmed System Five and the Acuson Power Vision.

Besides the scanners briefly described above, there exist other ultrasonic scanners, examples of which are disclosed in U.S. Pat. No. 4,134,554 and U.S. Pat. No. 4,315,435. Basically, these patent specifications relate to various techniques including dynamic cross-sectional echography (DCE) for producing sequential two-dimensional images of cross-sectional slices of animal or human anatomy by means of ultrasound energy at a frame rate sufficient to enable dynamic visualisation of moving organs. Types of apparatus utilised in DCE are generally called DCE scanners and transmit and receive short, sonic pulses in the form of narrow beams or lines. The reflected signals' strength is a function of time, which is converted to a position using a nominal sound speed, and is displayed on a cathode ray tube or other suitable devices in a manner somewhat analogous to radar or sonar displays. While DCE can be used to produce images of many organ systems including the liver, gall bladder, pancreas and kidney, it is frequently used for visualisation of tissue and major blood vessels of the heart.

The microcapsules may be used for imaging a wide variety of areas, even (if of less than about 8 μm) when injected at a peripheral venous site. Those areas include (without limitation): (1) the venous drainage system to the heart; (2) the myocardial tissue and perfusion characteristics during an exercise treadmill test or the like; and (3) myocardial tissue after an oral ingestion or intravenous injection of drugs designed to increase blood flow to the tissue. Additionally, the microcapsules may be useful in delineating changes in the myocardial tissue perfusion due to interventions such as (1) coronary artery vein grafting; (2) coronary artery angioplasty (balloon dilation of a narrowed artery); (3) use of thrombolytic agents (such as streptokinase) to dissolve clots in coronary arteries; or (4) perfusion defects or changes due to a recent heart attack.

Furthermore, at the time of a coronary angiogram (or a digital subtraction angiogram), an injection of the microcapsules may provide data with respect to tissue perfusion characteristics that may augment and complement the data obtained from the angiogram procedure, which identifies only the anatomy of the blood vessels.

Through the use of microcapsules according to the present invention, other non-cardiac organ systems including the liver, spleen and kidney that are presently imaged by ultrasonic techniques may be suitable for enhancement of such currently obtainable images, and/or the generation of new images showing perfusion and flow characteristics that have not previously been susceptible to imaging using prior art ultrasonic imaging techniques.

Following any interventional procedure, the reperfusion that subsequently occurs will usually take a minimum of 3 minutes to provide a stable image.

Reperfusion may still occur up to 24 hours after administration, i.e. perfusion changes in the myocardium may be monitored for up to 24 hours after interventional procedures.

The intervention may be surgical. Alternatively, it may involve the administration of a drug, e.g. a known thrombolytic agent such as urokinase.

As indicated above, by incorporating or linking drugs within, into or onto the microcapsule shell, it is possible to produce an imaging agent with therapeutic activity. This can be achieved by co-spray-drying the drug with a wall-forming material such as albumin (heterogeneous formulation) or by spray-drying the drug substance alone (homogeneous formulation). Drug-loaded microcapsules can also be produced by chemically cross-linking the drug onto the surface of pre-formed microcapsules. By controlling the level of stabilisation, it is possible to produce microcapsules with differing rates of biodegradation. Spray-drying conditions and materials, and drug loading/linking methods, are variously described in the WO publications identified above.

The ability to image and target therapeutic agents to specific sites in the myocardium and coronary arteries offers the potential to deliver accurately a wide range of drugs useful in the treatment of cardiovascular disease. The localised delivery of such drugs has the benefits of reducing both potential systemic toxicity and drug dose required.

The types of drugs that can be delivered in microcapsule form include the following:

a) Anti-platelet agents such as thromboxane synthase inhibitors, thromboxane $A_2$ antagonists, prostacyclin analogues, indobufen, ticlopidine hydrochloride and GpIIb/IIIa receptor antagonists.

b) Thrombin inhibitors such as heparin, low molecular weight heparins, heparinoids, argatroban, hirudin and hirulog.

c) Fibrinolytic agents such as tissue plasminogen activators (t-PAs) urinary plasminogen activators (u-PAs), second generation versions of plasminogen activators, hementin, streptokinase and staphylokinase. Such agents can act to break down clots, and to cause vasodilation and hence enhance blood flow.

d) Tissue factor inhibitors such as recombinant tissue pathway inhibitor.

e) Vasodilators including angiotensin-converting enzyme (ACE) inhibitors, such as enalaprilat, and forskolin; further, nitric oxide donors can be used, to inhibit platelet aggregation, to enhance blood flow and to mediate vasorelaxation. For example, tryptophan may be included in the feedstock for microparticles, and reacted with sodium nitrate, to give nitrosotryptophan; see Zhang et al (1996) J. Biol. Chem. 271:14271–9. Available cysteine (e.g. Cys-34 in HSA) may also be nitrosated, by the same means. Nitrosotryptophan is less stable than its corresponding thiol and should, therefore, be more reactive at its site of action, the endothelial cell membrane. Relatively "soft" microparticles (treated at 176° C. for 20 min) may associate better with the membrane surface.

f) Calcium channel blockers including verapamil and dihydropyridine derivatives such as elgodipine.

g) Potassium channel openers such as pinacidil and nicorandil.

h) Drugs with potential as anti-restenosis agents including cytochalasin B, protein kinase inhibitors, dexamethasone, anti-neoplastic agents, such as mitomycin C and methotrexate, angiopeptin, genes such as p21, retinoblastoma and vascular endothelial growth factor (VEGF) and antisense oligonucleotides such as LR-3280.

i) Drugs that induce the production of heat shock proteins (e.g. isoproterenol). Microparticles with such a drug may be delivered simultaneously with the same capsules lacking drug, to supplement the use of ultrasound to raise local temperature and induce the production of heat shock proteins. Ultrasound could be used to release the drug at the site of action. Further, delivery of microcapsules after an ischaemic event may be used to maintain levels of heat shock proteins and give cytoprotection against a second attack. The microcapsules may be delivered to the ischemic myocardium and be trapped by occlusions. This would allow controlled and continued protection of tissue at the required regions of the myocardium and may suppress other symptoms such as reperfusion injury and myocardial stunning (cf combined therapy using NO as a free radical scavenger during reperfusion).

To prolong the effects of heat shock proteins as cytoprotective agents, it is envisaged that the regulation of these proteins would require genetic control. The main problem with gene therapy for this treatment is the inability to target the cardiomyocytes or endothelial cells within the heart; see Gerard and Heidell (1993) Trends Cardiovasc. Med. 3:9–15. This therapy is a good candidate for parenteral gene delivery using defatted HSA microcapsules (see International Patent Application No. PCT/GB97/01970). Further, targeting may be improved by using a co-transcytosis factor, in association with a cationic lipid:plasmid complex carried by the defatted HSA vehicle, to interact with the endothelial membranes. Targeting of the myocardium and receptor-mediated uptake of DNA should improve transfection and could be applied to other coronary heart disease therapies.

j) NO-scavengers, or inhibitors of NO synthesis.
k) Antioxidants or free radical-scavengers (which may have the function of scavenging NO) such as glutathione, methionine, cystine or cysteine.
l) Antibiotics, e.g. for the treatment of endocarditis.

In addition or instead of the use of drugs that induce the production of heat shock proteins (see section (i) above), ultrasound or some other means may be used, when the microcapsules are located, to give a small, non-lethal rise in temperature, e.g. by 2–3° C., for the same effect. Thus, ultrasound may be used, both to image the heart/myocardium and as a targeted form of energy that is converted into heat by localised microcapsules. Imaging of the myocardium may therefore allow preconditioning of tissues susceptible to ischemic events, rather than preconditioning of the whole heart. Imaging may also be used to determine the presence of drug, and to quantify its potency, as a function of brightness.

Preferred aspects of the present invention will now be described by way of example. For use in the following Examples, albumin microcapsules, 6–15 $\mu$m in diameter, mean size c.10–11 $\mu$m, median size c.10–11 $\mu$m (by volume), were prepared by the procedures described in Example 1 of WO-A-9615184, except that larger microcapsules are obtainable by increasing the concentration of the albumin (to about 20% w/v) and by varying the inlet pressure appropriately. The ethanol is generally omitted.

The desired size range can be further refined by classifying the microcapsules after they have been formed, for example by flotation. In a homogeneous dispersion of microspheres, larger particles will rise to the surface faster than smaller particles due to the lower density (more encapsulated air) of the larger particles. Hence, by allowing the dispersion to stand, the particle size distribution will change at any level of the solution with respect to time.

Microspheres were dispersed in 2000 ml of aqueous solution containing 6% w/v sodium chloride and 0.1% w/v Pluronic F68 in a glass bottle giving a liquid column of approximately 165 mm. A sampling tube was placed 50 mm below the upper liquid surface to enable removal of samples at timed intervals.

By altering the standing time and sodium chloride concentration, it was possible to produce a variety of particle size distributions and classify microspheres down to 2 $\mu$m. other wet techniques for classification include hydrodynamic chromatography and field flow fractionation. 'Dry' techniques using the principles of elutriation and cross flow separation are commercially available in the form of the Microsplit (British Rem.), Zig-zag (Alpine) and Turbo (Nissuin) classifiers. The elbow jet classifier produced by Nitettsu Mining Co uses a different principle (the Coanda Effect) which could also achieve good results for the classification of microspheres.

EXAMPLE 1

Emergency percutaneous transluminal coronary angioplasty (PTCA) procedures are carried out when it is expected that a large risk area/large infarction is present. The patient is transferred to the coronary care setting and a catheter inserted into the left ventricle. A 5 ml dose of $1.5 \times 10^7$ albumin microcapsules per ml is administered into the left atrium and flushed from the catheter with 5 ml of saline. Five minutes after administration of the microcapsules, a 3-D image of the heart is obtained using an ATL 3000 HD1 ultrasound machine, images being gathered using a P5-3 ultrasound probe operating in the harmonic (continuous) mode.

Multiplane images are gathered and a 3-D reconstruction of the heart is obtained, using a TomTek rotational device. From this initial study, the risk volume is accurately determined.

The risk area being confirmed, PTCA is carried out on the affected coronary artery. This procedure can be carried out within 5–10 minutes of the injection of the microcapsules or up to 24 hours after the injection.

Following PTCA, successful re-flow in the risk area can then be confirmed by echocardiographic examination for up to 24 hours, without further injection of the microcapsules. The catheter can be removed immediately after the procedure.

EXAMPLE 2

Interventional therapy relating to a large risk area in the apical region of the heart is relatively difficult, since this region is supplied by more than one major coronary artery vessel. Following the initial administration of 5 ml of the albumin microcapsules, the assessment of risk volume in the apical region is made by echocardiographic examination. Again, an ATL 3000 HD1 ultrasound machine is used in conjunction with a TomTek rotational device.

To restore normal flow to the apical region of the myocardium, a sequential 2–3 step PTCA procedure is performed. Successful intervention is confirmed by the reperfusion of the microcapsules (confirmed by echogenic examination as described above) over a period of 15–60 minutes after intervention.

Hence, the microcapsules will provide valuable information on whether to continue with the PTCA procedure in other vessels, or whether "normal" flow has returned to the apical region.

EXAMPLE 3

In Examples 1 and 2, the reperfusion properties of the microcapsules are used to determine the successful outcome of PTCA procedures. A further advantage is in the calculation of infarct volume.

In an experimental study, open-chested dogs had selected coronary artery occlusions inflicted. Each dog had either the left circumflex (LCX) or the left anterior descending (LAD) coronary artery occluded for up to 4 hours.

A single dose of the albumin microcapsules (5–10 ml) was administered into the left atrium and the risk volume was calculated by 3-D echocardiography as described above. Prior to release of the occlusion, $Tc^{99m}$ microcapsules were administered by the same route.

After 2–4 hours, the occlusion was released and the heart examined by 3-D echocardiography once again, for periods up to 3 hours post-occlusion release. The albumin microcapsules clearly reperfused back into the risk area but complete opacification was not achieved. The non-perfused region corresponded to the infarct volume which, once again, could be accurately determined by 3-D echocardiographic examination. This calculation was possible without further injections of agent being required.

After sacrifice, the accuracy of the determination of risk volume and infarct volume was undertaken by slicing the heart into 0.9 mm slices. The risk area was calculated by $Tc^{99m}$ autoradiography and gave excellent correlation with the risk area calculated by the method above (g=1.02+1.1, r=0.90, p=<0.001, SEE=2.5). The reperfusion properties of the microcapsules were used to determine infarct volume. Once again, excellent correlation was obtained between infarct volume calculated by 3D echocardiographic evaluation and actual infarct volume calculated from the slices using triphenyl tetrazolium chloride (TTC) tissue staining.

We claim:

1. A diagnostic method which comprises the steps of
    (i) administering hollow microcapsules into a blood vessel of a patient having a perfusion defect;
    (ii) treating the patient, to remove an occlusion at least partially, such that blood flow in at least one area of tissue affected by the defect is increased; and
    (iii) obtaining an ultrasonic image of the tissue post-treatment.

2. A method according to claim 1, wherein the treatment is surgical.

3. A method according to claim 1, wherein the treatment is by thrombolysis.

4. A method according to claim 1, which additionally comprises obtaining ultrasonic images of the tissue substantially continuously, to provide a real-time visualisation of the tissue before, during and after the treatment.

5. A method according to claim 1, wherein said administering step consists of a single administration of said microcapsules before said treatment.

6. A method according to claim 1, wherein the tissue is cardiac tissue, especially the myocardium.

7. A method according to claim 1, wherein the microcapsules are obtained or obtainable by spray-drying a solution of a wall-forming material.

8. A method according to claim 7, wherein the wall-forming material is a protein.

9. A method according to claim 8, wherein the protein is albumin.

10. A method according to claim 1, wherein the microcapsules have a diameter of 1–20 μm, with a median diameter of 6–15 μm.

11. A diagnostic method according to claim 1, which further comprises obtaining an ultrasonic image of said tissue prior to said treatment.

12. A method for diagnosing, by ultrasonic imaging, the effect of treatment of an occlusion in a patient having a perfusion defect, said method comprising:
    (i) administering to said patient hollow microcapsules capable of being retained in capillary beds, before said treatment; and
    (ii) obtaining an ultrasonic image of tissue affected by said perfusion defect post-treatment.

13. A method for obtaining ultrasonic images of tissue of a patient having a perfusion defect, said method comprising:
    (i) administering hollow microcapsules to said patient; and
    (ii) obtaining an ultrasonic image of said tissue, wherein said images are obtained before and after treatment of an occlusion in said patient.

14. A method according to claim 12 or 13, wherein said treatment is surgical.

15. A method according to claim 12 or 13, wherein said treatment is by thrombolysis.

16. A method according to claim 12 or 13, wherein a drug is incorporated or linked in, on or onto said microcapsules.

17. A method for treating tissue having a perfusion defect comprising administering a therapeutically effective amount of hollow microcapsules to said tissue before treatment of an occlusion in said tissue, wherein said microcapsules are capable of being retained in capillary beds and have a drug bound thereto.

18. A method according to claim 12 or 13, wherein the tissue is cardiac tissue.

19. A method according to claim 18, wherein the tissue is the myocardium.

20. A method according to claim 12, 13 or 17, wherein said microcapsules are obtained by spray-drying a solution of a wall-forming material.

21. A method according to claim 20, wherein said wall-forming material is a protein.

22. A method according to claim 21, wherein said protein is albumin.

23. A method according to claim 12, 13 or 17, wherein said microcapsules have a diameter of 1–20 μm, with a median diameter of 6–15 μm.

* * * * *